United States Patent [19]

Csatary

[11] Patent Number: 5,602,023

[45] Date of Patent: Feb. 11, 1997

[54] PHARMACEUTICAL PRODUCT CONTAINING LIVE, STABILIZED VIRUS FOR THE THERAPY OF VIRAL AND MALIGNANT DISEASES AND PROCESS FOR PREPARING THE SAME

[76] Inventor: Laszlo K. Csatary, 2100 S. Ocean La., #2503, Fort Lauderdale, Fla. 33316

[21] Appl. No.: 302,873

[22] PCT Filed: Mar. 23, 1993

[86] PCT No.: PCT/US93/02441

§ 371 Date: Nov. 2, 1994

§ 102(e) Date: Nov. 2, 1994

[87] PCT Pub. No.: WO93/18790

PCT Pub. Date: Sep. 30, 1993

[30] Foreign Application Priority Data

Mar. 24, 1992 [HU] Hungary .......................... 976/92/9669
Aug. 17, 1992 [HU] Hungary ........................ 976/92/26547

[51] Int. Cl.$^6$ ..................................................... C12N 7/04
[52] U.S. Cl. .................. 435/236; 424/184.1; 424/211.1; 424/214.1; 424/215.1; 424/222.1; 424/229.1; 424/233.1; 435/239
[58] Field of Search ........................... 424/184.1, 211.1, 424/214.1, 215.1, 222.1, 229.1, 233.1; 435/239, 236

[56] References Cited

U.S. PATENT DOCUMENTS

3,874,999  4/1975  Zaremba et al.
5,124,148  6/1992  Csatary et al. ...................... 424/281.1

FOREIGN PATENT DOCUMENTS

2070903  12/1992  Canada.
0138667  4/1985  European Pat. Off.
8600529  1/1986  WIPO.
8600811  2/1986  WIPO.
8800980  2/1988  WIPO.
9118089  11/1991  WIPO.
9300807  1/1993  WIPO.

OTHER PUBLICATIONS

Mackett, M., et al., *DNA Cloning* vol. II, Chapter 7, pp. 191–211, Glover, D. M. ed. (1985).

Database Medline Abstract No. 79079695, UEBA "Respiratory Synctyial Virus. I.Concentration And Purification Of The Infectious Virus" *Acta Med Okayama* (1978 Aug.) 32 (4), 265–72 (abstract).

Database Medline Abstract No. 84027734, Williams, "The Surface Activity of PVP and Other Polymers and Their Antihemolytic Capacity" *Cryobiology* (1983 Oct.) 20 (5) 521–6 (abstract).

Database WPI, Section Ch, Week 9039, Derwent Publications Ltd., London, GB; AN 90–292811 & HU–A–52 812 (Phylaxia Oltoanyagt) (abstract).

Database WPI, Section Ch. Week 8609, Derwent Publications Ltd., London, GB; AN 86–055952 & DD–A–229031 (Forsch Lungen Tuber) (abstract).

Database WPI, Section Ch, Week 8435, Derwent Publications Ltd., London, GB; AN 84–215368 & HU–A–32250 (Phylaxia Oltoanyag) (abstract).

Preblud et al, "Measles Vaccine" in *Vaccines* Plotkin et al eds. W. B. Saunders Co, Philadelphia, PA 1988 pp. 182–222.

Brakke et al "Miscellaneous Problems in Virus Purification" in *Methods in Virology*, vol. II Academic Press, N.Y, 1967, pp. 119–136.

Kuchler R. J. "Virus Growth & Purification" in *Biochemical Methods in Cell Culture and Virology*, Dowden, Huchington & Ross, Inc. Stroudsburg, PA 1977, pp. 168–205.

*Primary Examiner*—James C. Housel
*Assistant Examiner*—Khalid Masood
*Attorney, Agent, or Firm*—Sixbey, Friedman, Leedom & Ferguson, PC; Stuart J. Friedman

[57] ABSTRACT

A process for preparing a purified virus vaccine comprises the steps of purifying a fluid containing a virus by centrifugation, ultracentrifuging to pellet the supernatant, purifying the virus by sucrose gradient ultracentrifugation, rehydration and lyophilization. Desirably, a modified starch, such as hydroxyethyl starch having a molecular weight in the range 100,000–300,000, is added as a protective colloid prior to lyophilization. The virus is selected from the group consisting of avian paramyxovirus, avian herpesvirus, avian rotavirus, avian bronchitis, avian encephalitis, avian bursiris (Gumboro) virus, Marek's disease virus, parvovirus, Newcastle disease virus, human paramyxovirus, human parvovirus, human adenovirus, and mixtures thereof. A purified virus vaccine made by the foregoing method is useful for the treatment and control of mammalian disease of viral origin.

11 Claims, No Drawings

PHARMACEUTICAL PRODUCT CONTAINING LIVE, STABILIZED VIRUS FOR THE THERAPY OF VIRAL AND MALIGNANT DISEASES AND PROCESS FOR PREPARING THE SAME

The present invention relates to pharmaceutical products containing stabilized, live virus for the therapy of viral diseases and malignancies and to the process for the production of such products. The present invention also relates to a purified virus vaccine and the purification procedure therefor.

Hungarian Patents #197 517 and #197 846 describe the use of certain live, apathogenic viruses in the therapy of various human diseases of vital origin. Thus, patent #197 517 provides a pharmaceutical product containing attenuated Newcastle disease virus suitable for the therapy of herpes, rabies, AIDS and malignancies. Patent #197 846 describes a pharmaceutical product containing attenuated Gumboro virus suitable for the treatment of hepatitis, rabies, and other diseases of viral origin and malignancies. Although both Gumboro and Newcastle disease viruses cause poultry diseases, the vaccines containing these attenuated viruses are in commercial use. The above patents describe the therapeutic application of these vaccines.

Since the purity of veterinary vaccines do not meet human purity requirements, infections and complications may result as untoward side effects. Moreover, the stability of veterinary vaccines may also be poor. The present invention is intended to provide a process to obtain purified, apathogenic viruses suitable for human therapy as well as a lyophilized product which is stable for long periods without apparent loss of effectiveness.

Recently, it has been found that other apathogenic viruses can also be used in the therapy of human diseases of vital origin. It has been proven, according to the present invention, that any attenuated virus apathogenic for humans can be used, alone or in combination, in the treatment of viral diseases. These may be veterinary, in particular, fowl viruses, or human viruses; e.g.; arian paramyxovirus, avian herpesvirus, avian rotavirus, avian bronchitis, avian encephalitis, avian bursitis (Gumboro) virus, Marek's disease virus, parvovirus, Newcastle disease virus as well as human paramyxovirus, human parvovirus and human adenovirus.

The invention relates to attenuated viruses apathogenic to humans which are effective in the treatment of diseases of viral origin and malignancies, e.g., as follows: AIDS, carcinoma of the rectum, bladder, breast, colon, cervix, esophagus, pancreas, bronchus, liver, kidney and stomach, gynecological cancers, head and neck cancers, lymphomas, malignant melanoma, myeloma, immune deficiency due to irradiation, multiple sclerosis, influenza, common cold and related diseases of viral origin, herpes genitalis and labialis, warts, collagen diseases, acute and chronic hepatitis (B and C), and symptoms following bone marrow transplantation.

The viruses suitable for the above therapeutic purposes may be obtained as usual, e.g., from fibroblast or other cell line cultures or allanto-amniotic fluid of egg embryos. The allanto-amniotic fluid can be obtained from infected hen eggs. The fluid is purified by centrifugation and the supernatant is pelleted by ultracentrifuge. The sediment is rehydrated and sedimented over sucrose gradient, ultracentrifuged again and the pellet is rehydrated and lyophilized.

In a preferred embodiment of the invention the allantois fluid is centrifuged by approximately $5000 \times g$, the pellet is discarded and the supernatant is used (if necessary a filtration step can be included). The virus is pelleted from this supernatant by ultracentrifugation (the ultracentrifugation depends on the r.p.m. and time, and may vary over a wide range, usually $35,000 \times g$ for 1 hour). The supernatant is discarded and the pellet is resuspended in a small volume of buffer solution. For appropriate homogeneity a relative longer period of mixing is required.

This homogeneous suspension is layered over a high concentration of sucrose and ultracentrifuged at $90,000$–$100,000 \times g$ (minimal g: 60,000). The supernatant is discarded and the pellet is rehydrated and lyophilized.

Another object of the invention is stabilization of the virus preparation. Protective colloids, either alone or in combination, during lyophilization are generally used in the production of vaccines. Such colloids are, e.g., milk (3–10%), polyvinylpyrrolidone and gelatin (0.1–0.2%), and glucose, sucrose or dextran (1–10%). However, for human use, these colloids are either unsatisfactory or may cause side effects.

We have found that modified starch, either alone or in combination, can preferably be used as the protective colloid, such as hydroxyethyl starch (molecular weight: 100,000–300,000). Hydroxyethyl-starch of an average molecular weight of 200,000 is used as plasma expander, but such compounds have not been used as protective colloids for vaccine production.

The new stabilized product according to this invention contains, together with other compounds, an effective mount of modified starch as the protective colloid.

The invention will be detailed in the following examples. Newcastle disease and Gumboro virus can be purchased from Phylaxia of Budapest, Hungary as PHYLAVAC and GUMBOPHYL, respectively.

EXAMPLE #1

Purification of Newcastle disease virus from allantois fluid

Three liters of allanto-amniotic fluid containing the virus were centrifuged at $5000 \times g$ for 1 hour. The supernatant was faltered through multiple layers of gauze. The virus was pelleted from the supernatant by ultracentrifugation (SCP 85 H2 ultracentrifuge, RP 19 rotor, 18,500 rpm ($35,000 \times g$, $4°$ C., 1 h)). After discarding the supernatant, the pellet was resuspended in 30 ml NTE buffer (0.15M NaCl, 0.001M EDTA, 0.05M TRIS; pH 7.4). The suspension was gently mixed for 24 hours in an ice bath.

The suspension was further purified by sucrose gradient ultracentrifugation. Thirty ml of 30% (w/w) (=33 % w/v) sucrose in NTE buffer was placed into centrifuge tubes and 5 ml of suspension was layered onto the sucrose. The tubes were ultracentrifuged in an SRP rotor at $95,000 \times g$ (27,500 rpm) for 80 min.

After discarding the supernatants, the pellets were resuspended in NTE buffer (0.5 ml/tube). The collected supernatants were gently mixed for 24 hours in an ice bath.

The concentration of virus during the purification procedure was checked by neuraminidase activity, hemagghtination and ELISA. The infectivity of the virus was measured by the inoculation of preincubated eggs. The protein concentration was measured by-the method of Spector. The purity of the product was checked by SDS gel electrophoresis; except for HN, NP and M proteins no other bands (contaminants) should be seen.

The above method displayed the following features:

|  | Volume | ELISA (HI) | yield % |
| --- | --- | --- | --- |
| Original material | 3 l | 154 | 100 |
| Supernatant | 3 l | 1 | 0.06 |
| Resuspended pellet | 42 ml | 9531 | 87 |

-continued

|  | Volume | ELISA (HI) | yield % |
|---|---|---|---|
| Supernatant over sucrose | 310 ml | 467 | 31 |
| Purified virus | 11 ml | 20803 | 50 |

EXAMPLE #2

Purification of Gumboro virus from Vero cell culture 2300 ml supernatant of Vero cell culture was centrifuged for 30 min at 5000× g at 4° C. Virus was pelleted from the supernatant by ultracentrifugation (SCP 85 H2 ultracentrifuge, RP 19 rotor, 18,500 rpm (35,000× g, 4° C., 1 h)). After discarding the supernatant, the pellets were resuspended in 23 ml NTE buffer (1% of the original volume). The suspension was gently mixed for 24 hours in an ice bath.

The suspension was further purified by sucrose gradient ultracentrifugation. Thirty ml of 30% (w/w) (=33 % w/v) sucrose in NTE buffer was placed into centrifuge robes and 5 ml of suspension was layered onto the sucrose. The robes were ultracentrifuged in SRP 288A rotor at 95,000× g (27,500 rpm) for 80 min.

After discarding the supernatants, the pellets were resuspended in NTE buffer (1 ml/tube), then washed with 1 ml buffer. The collected supernatants were gently mixed for 24 hours in an ice bath.

The concentration of virus during the purification procedure was checked by ELISA. The infectivity of the virus was measured by its cytopathogenic effect. The protein concentration was measured by the method of Spector.

The above described method displays the following features:

|  | volume | ELISA (HI) | yield % |
|---|---|---|---|
| Original material | 2300 ml | 171 | 100 |
| After centrifugation | 2300 ml | 133 | 78 |
| Supernatant | 2300 ml | 48 | 28 |
| Resuspended pellet | 28 ml | 3621 | 26 |
| Supernatant over sucrose | 180 ml | 212 | 10 |
| Purified virus | 13 ml | 5271 | 17 |

EXAMPLE #3

Stabilized virus for human therapeutic use 2-2 % (v/v) glucose, sucrose and hydroxyethyl-starch (mw: 200,000) (ISOHES, HES 200/0.5) were added to the virus suspension obtained from example #1, then lyophilized. After reconstitution, even after prolonged storage, the original ELISA titre was obtained.

I claim:

1. A highly purified stable vaccine suitable for administration to humans produced from a live, stabilized virus apathogenic to humans comprising arian bursitis virus or Newcastle disease virus stabilized with an effective amount of a protective colloid comprising a modified starch.

2. The highly purified stable vaccine described in claim 1, wherein said protective colloid is hydroxyethyl starch having an average molecular weight of 100,000 to 300,000.

3. The highly purified stable vaccine described in claim 1, wherein said effective amount of a protective colloid includes glucose and sucrose and hydroxyethyl starch having a molecular weight of 200,000.

4. A method for producing a stable vaccine with a purity suitable for human administration from a selected virus apathogenic to humans or a selected virus pathogenic to humans, comprising:

(a) obtaining a fluid containing the selected virus;

(b) subjecting the virus-containing fluid to selected centrifugation or ultracentrifugation steps appropriate for the selected virus to separate the virus from said fluid and to produce a virus-containing pellet;

(c) forming a homogeneous virus-containing suspension from said pellet in a buffer solution;

(d) purifying the virus-containing suspension by sucrose gradient ultracentrifugation to produce a purified virus-containing pellet;

(e) producing a purified virus suspension from said purified virus-containing pellet;

(f) stabilizing the purified virus suspension by adding an effective amount of a protective colloid comprising hydroxyethyl starch with a molecular weight of 100,000 to 300,000 to said suspension; and (g) lyophilizing the stabilized purified virus suspension to produce a stable, highly pure vaccine suitable for administration for humans.

5. The method described in claim 4, wherein the fluid containing the selected virus is obtained from a fluid source selected from the group consisting of fibroblast culture supernatants, cell line culture supernatants and allantoamniotic fluid.

6. The method described in claim 4, wherein said stabilizing compound comprises a modified starch which behaves toward said virus like a protective colloid.

7. The method described in claim 6, wherein said modified starch is hydroxyethyl starch having a molecular weight of 100,000 to 300,000.

8. The method described in claim 4, wherein said virus is apathogenic to humans and is selected from the group consisting of avian paramyxovirus, avian herpesvirus, avian rotavirus, avian bronchitis virus, avian encephalitis virus, avian bursitis (Gumboro) virus, Marek's disease virus, parvovirus, Newcastle disease virus and mixtures thereof.

9. The method described in claim 4, wherein said virus is pathogenic to humans and is selected from the group consisting of human paramyxovirus, human parvovirus, human adenovirus and mixtures thereof.

10. A stable vaccine produced according to the method of claim 8.

11. A stable vaccine produced according to the method of claim 9.

* * * * *